US011699505B2

(12) United States Patent
Kanamarlapudi et al.

(10) Patent No.: US 11,699,505 B2
(45) Date of Patent: Jul. 11, 2023

(54) METHOD AND SYSTEM FOR ESTIMATING CORROSION INHIBITOR CONCENTRATION USING A MULTI-ELECTRODE ARRAY SENSOR

(71) Applicant: Tata Consultancy Services Limited, Mumbai (IN)

(72) Inventors: Venkata Muralidhar Kanamarlapudi, Pune (IN); Naga Neehar Dingari, Pune (IN); Parijat Deshpande, Pune (IN); Jayita Dutta, Pune (IN); Soumyadipta Maiti, Pune (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 403 days.

(21) Appl. No.: 16/699,518

(22) Filed: Nov. 29, 2019

(65) Prior Publication Data
US 2020/0176088 A1   Jun. 4, 2020

(30) Foreign Application Priority Data

Nov. 29, 2018  (IN) .............................. 201821045160

(51) Int. Cl.
*G16C 20/70* (2019.01)
*G01N 17/02* (2006.01)
*G06N 20/00* (2019.01)
*G06N 7/01* (2023.01)

(52) U.S. Cl.
CPC ............. *G16C 20/70* (2019.02); *G01N 17/02* (2013.01); *G06N 7/01* (2023.01); *G06N 20/00* (2019.01)

(58) Field of Classification Search
CPC ........ G16C 20/70; G06N 20/00; G06N 7/005; G01N 17/02
See application file for complete search history.

(56) References Cited

U.S. PATENT DOCUMENTS 376,844 A * 1/1888 Appert
2005/0274628 A1 12/2005 Yang
(Continued)

FOREIGN PATENT DOCUMENTS

CN  102426183 A * 4/2012
JP  H08271577 A * 10/1996 ............. G01R 31/26

OTHER PUBLICATIONS

Ebrahimi et al. ,Prediction aluminum corrosion inhibitor efficiency using artificial neural network (ANN), Ebrahimi et al., International Conference on Chemical Engineering and Bioprocess Engineering IOP Publishing , IOP Conf. Series: Earth and Environmental Science 36 (2016) (Year: 2016).*

(Continued)

*Primary Examiner* — Eman A Alkafawi
*Assistant Examiner* — Aeysha N Sultana
(74) *Attorney, Agent, or Firm* — Finnegan, Henderson, Farabow, Garrett & Dunner, LLP

(57) ABSTRACT

There is a demand for low-cost robust method to detect corrosion for estimating corrosion inhibitor (CI) concentration sensing. This disclosure herein relates to method and system for estimating corrosion inhibitor (CI) concentration using a multi-electrode array sensor. The method initially obtains a plurality of electrochemical signals using the multi-electrode array sensor from the corroding environment. Further, the plurality of electrochemical signals are analyzed to obtain a plurality of parameters. Further, the method analyses a plurality of features from the plurality of parameters for estimating the corrosion inhibitor (CI) concentration using a trained machine learning model. The method is capable of estimating the corrosion inhibitor concentration of any unknown liquid using the regression model and the classification model.

7 Claims, 7 Drawing Sheets

(56) References Cited

U.S. PATENT DOCUMENTS

| | | | | |
|---|---|---|---|---|
| 2009/0279073 | A1* | 11/2009 | Sardashti | G01N 21/658 356/73 |
| 2011/0044524 | A1* | 2/2011 | Wang | G01R 33/54 382/131 |
| 2012/0132541 | A1* | 5/2012 | Kipouros | G01N 17/02 205/776.5 |
| 2014/0026648 | A1* | 1/2014 | Schmitz | G05D 21/02 73/61.59 |
| 2014/0326340 | A1* | 11/2014 | Kuriki | C23F 11/00 137/565.11 |
| 2015/0205000 | A1* | 7/2015 | Perkins | G01V 8/10 702/8 |
| 2016/0139030 | A1 | 5/2016 | Jovancicevic et al. | |
| 2016/0161425 | A1* | 6/2016 | Berezin | G01N 33/2823 324/638 |

OTHER PUBLICATIONS

Hosseinibalajadeh, Lead corrosion Inhibitors in Drinking water, Aug. 2018 (Year: 2018).*

A. Turnbull et al., "A Multi-Electrode Approach to Evaluating Inhibition Of Under deposit Corrosion In CO2 Environments", NACE-09445,Jan. 2009, NACE International, https://www.onepetro.org/conference-paper/NACE-09445.

David A. Winkler, "Predicting the Performance of Organic Corrosion Inhibitors", Metals—Open Access Journal, Dec. 2017, Volume-issue Nos. 7(12), Metals—Open Access Journal https://www.mdpi.com/2075-4701/7/12/553#versions-div.

* cited by examiner

METHOD AND SYSTEM FOR ESTIMATING CORROSION INHIBITOR CONCENTRATION USING A MULTI-ELECTRODE ARRAY SENSOR

This U.S. Patent application claims priority under 35 U.S.C § 119 to Indian patent application no. (201821045160), filed on Nov. 29, 2018. The entire contents of the aforementioned application are incorporated herein by reference.

TECHNICAL FIELD

The disclosure herein generally relates to sensing of corrosion inhibitor concentration, and, more particularly, to method and system for estimating corrosion inhibitor concentration using a multi-electrode array sensor.

BACKGROUND

Corrosion means environmental deterioration or degradation of metals, which hinders their intended usage and reduces life span of engineering components. Corrosion Inhibitor dosing is a preventive measure against corrosive attack on metallic materials. The presence of corrosion media in liquid fuel, oil, natural gas, water pipelines and thereof degrades the useful properties of materials and structures including strength, reliability, efficient operation of equipment and structures which complicates the vicinity of engineering components. Further, corrosion inhibitor dosing techniques are widely used in many industries like oil and gas, water treatment, chemical processing plants etc. for preventing corrosion in engineering components like storage tanks, parts of processing plants and pipelines. However, in addition to being expensive, corrosion inhibitors add to the contamination of the end-products, removal of which incurs additional cost. Further, they may be ineffective or counter-productive beyond a certain concentration. In such scenarios, precise monitoring of corrosion inhibitor concentration can help industries for developing a feedback-based control system for dosing inhibitors. Therefore, a method to detect the presence of corrosion inhibitor in-situ is necessary and accurately quantifying them is required.

Most of the conventional techniques provide solutions that can detect corrosion inhibitors, are expensive, and accuracy seems a challenge. These conventional techniques involve expensive and cumbersome chromatography, spectroscopy and fluorescence techniques. In addition, these methods are mostly practiced and standardized for pre-defined ambient laboratory conditions. Therefore, these methods lack deployment in dynamic corroding environment and in tough conditions of the industry. Thus, a technique for estimating corrosion at which material corrodes is required to ensure the measuring of detected corrosion rate accurately.

SUMMARY

Embodiments of the present disclosure present technological improvements as solutions to one or more of the above-mentioned technical problems recognized by the inventors in conventional systems. For example, in one embodiment, a system for is provided. The system includes a processor, an Input/output (I/O) interface and a memory coupled to the processor is capable of executing programmed instructions stored in the processor in the memory to position a multi-electrode array sensor in a corroding environment for estimating a corrosion inhibitor (CI) concentration associated with a liquid media from the corroding environment. Further, the plurality of electrochemical signals using the multi-electrode array sensor are obtained from the corroding environment. The plurality of electrochemical signals are analyzed to obtain a plurality of parameters comprising an electrochemical impedance spectra and a DC current versus time. Further, the system identifies a plurality of features from the plurality of parameters comprising a charge transfer resistance feature obtained from the impedance spectra parameter, and an initial DC current and an intermediate DC current which are obtained from the DC current versus time. Furthermore, the corrosion inhibitor (CI) concentration from the plurality of features are estimated using a trained machine learning model comprising, a regression model, determining a quantitative estimate of the corrosion inhibitor (CI) concentration, wherein the regression model is trained using a training dataset utilized as a ground truth to determine the quantitative estimate of the corrosion inhibitor (CI) concentration. The classification model, determining a qualitative estimate of the corrosion inhibitor (CI) concentration, wherein the classification model is trained using the training dataset utilized as the ground truth to determine the qualitative estimate of the corrosion inhibitor (CI) concentration.

In one embodiment, the regression model is trained for determining the quantitative estimate of the corrosion inhibitor (CI) concentration by obtaining the plurality of features comprising the charge transfer resistance feature, the initial DC current and the intermediate DC current. The corrosion inhibitor (CI) concentration is determined for quantitative estimate from the plurality of features by, computing, a cost function using a pre-defined initial weightage factor 6 corresponding to the plurality of features, the training dataset and measure of error for fitting the cost function. Further, the computed cost function corresponding to the plurality of features is minimized based on a learning rate $\alpha$, a weightage factors $\theta_j$ for the plurality of features and the total number of iterations performed for the cost function. Further, the regression model determined a final weightage factors corresponding to the plurality of features. Further, the determined quantitative estimate of the corrosion inhibitor (CI) concentration is compared with a reference corrosion inhibitor (CI) concentration of the regression model.

In one embodiment, the classification model is trained for determining the qualitative estimate of the corrosion inhibitor (CI) concentration comprises obtaining, the plurality of features comprising the charge transfer resistance feature, the initial DC current and the intermediate DC current from the plurality of parameters. Further, the corrosion inhibitor (CI) concentration are determined for qualitative estimate from the plurality of features by, computing, a cost function using a logistic function, a pre-defined initial weightage factors $\theta$ corresponding to the plurality of features, the training dataset and a measure of error in fitting the cost function. Further, the computed cost function corresponding to the plurality of features are minimized based on a learning rate ($\alpha$), a weightage factors $\theta_j$ for the plurality of features and the total number of iterations performed for the cost function. Further, a final weightage factors corresponding to the plurality of features are determined. Further, the determined qualitative estimate of the corrosion inhibitor (CI) concentration is compared with a reference corrosion inhibitor (CI) concentration of the classification model.

In another aspect, provides a method that includes a processor, an Input/output (I/O) interface and a memory coupled to the processor is capable of executing programmed instructions stored in the processor in the memory to position a multi-electrode array sensor in a corroding environment for estimating a corrosion inhibitor (CI) concentration associated with a liquid media from the corroding environment. Further, the plurality of electrochemical signals using the multi-electrode array sensor are obtained from the corroding environment. The plurality of electrochemical signals are analyzed to obtain a plurality of parameters comprising an electrochemical impedance spectra and a DC current versus time. Further, the method identifies a plurality of features from the plurality of parameters comprising a charge transfer resistance feature obtained from the impedance spectra parameter, and an initial DC current and an intermediate DC current which are obtained from the DC current versus time. Furthermore, the corrosion inhibitor (CI) concentration from the plurality of features are estimated using a trained machine learning model comprising, a regression model, determining a quantitative estimate of the corrosion inhibitor (CI) concentration, wherein the regression model is trained using a training dataset utilized as a ground truth to determine the quantitative estimate of the corrosion inhibitor (CI) concentration. The classification model, determining a qualitative estimate of the corrosion inhibitor (CI) concentration, wherein the classification model is trained using the training dataset utilized as the ground truth to determine the qualitative estimate of the corrosion inhibitor (CI) concentration.

In one embodiment, the regression model is trained for determining the quantitative estimate of the corrosion inhibitor (CI) concentration by obtaining the plurality of features comprising the charge transfer resistance feature, the initial DC current and the intermediate DC current. The corrosion inhibitor (CI) concentration is determined for quantitative estimate from the plurality of features by, computing, a cost function using a pre-defined initial weightage factor $\theta$ corresponding to the plurality of features, the training dataset and measure of error for fitting the cost function. Further, the computed cost function corresponding to the plurality of features is minimized based on a learning rate $\alpha$, a weightage factors $\theta_j$ for the plurality of features and the total number of iterations performed for the cost function. Further, the regression model determined a final weightage factors corresponding to the plurality of features. Further, the determined quantitative estimate of the corrosion inhibitor (CI) concentration is compared with a reference corrosion inhibitor (CI) concentration of the regression model.

In one embodiment, the classification model is trained for determining the qualitative estimate of the corrosion inhibitor (CI) concentration comprises obtaining, the plurality of features comprising the charge transfer resistance feature, the initial DC current and the intermediate DC current from the plurality of parameters. Further, the corrosion inhibitor (CI) concentration are determined for qualitative estimate from the plurality of features by, computing, a cost function using a logistic function, a pre-defined initial weightage factors $\theta$ corresponding to the plurality of features, the training dataset and a measure of error in fitting the cost function. Further, the computed cost function corresponding to the plurality of features are minimized based on a learning rate ($\alpha$), a weightage factors $\theta_j$ for the plurality of features and the total number of iterations performed for the cost function. Further, a final weightage factors corresponding to the plurality of features are determined. Further, the determined qualitative estimate of the corrosion inhibitor (CI) concentration is compared with a reference corrosion inhibitor (CI) concentration of the classification model.

In yet another aspect, a non-transitory computer readable medium having embodied thereon a computer program for executing a method for positioning a multi-electrode array sensor in a corroding environment for estimating a corrosion inhibitor (CI) concentration associated with a liquid media from the corroding environment. Further, the plurality of electrochemical signals using the multi-electrode array sensor are obtained from the corroding environment. The plurality of electrochemical signals are analyzed to obtain a plurality of parameters comprising an electrochemical impedance spectra and a DC current versus time. Further, the method identifies a plurality of features from the plurality of parameters comprising a charge transfer resistance feature obtained from the impedance spectra parameter, and an initial DC current and an intermediate DC current which are obtained from the DC current versus time. Furthermore, the corrosion inhibitor (CI) concentration from the plurality of features are estimated using a trained machine learning model comprising, a regression model, determining a quantitative estimate of the corrosion inhibitor (CI) concentration, wherein the regression model is trained using a training dataset utilized as a ground truth to determine the quantitative estimate of the corrosion inhibitor (CI) concentration. The classification model, determining a qualitative estimate of the corrosion inhibitor (CI) concentration, wherein the classification model is trained using the training dataset utilized as the ground truth to determine the qualitative estimate of the corrosion inhibitor (CI) concentration.

In one embodiment, the regression model is trained for determining the quantitative estimate of the corrosion inhibitor (CI) concentration by obtaining the plurality of features comprising the charge transfer resistance feature, the initial DC current and the intermediate DC current. The corrosion inhibitor (CI) concentration is determined for quantitative estimate from the plurality of features by, computing, a cost function using a pre-defined initial weightage factor $\theta$ corresponding to the plurality of features, the training dataset and measure of error for fitting the cost function. Further, the computed cost function corresponding to the plurality of features is minimized based on a learning rate $\alpha$, a weightage factors $\theta_j$ for the plurality of features and the total number of iterations performed for the cost function. Further, the regression model determined a final weightage factors corresponding to the plurality of features. Further, the determined quantitative estimate of the corrosion inhibitor (CI) concentration is compared with a reference corrosion inhibitor (CI) concentration of the regression model.

In one embodiment, the classification model is trained for determining the qualitative estimate of the corrosion inhibitor (CI) concentration comprises obtaining, the plurality of features comprising the charge transfer resistance feature, the initial DC current and the intermediate DC current from the plurality of parameters. Further, the corrosion inhibitor (CI) concentration are determined for qualitative estimate from the plurality of features by, computing, a cost function using a logistic function, a pre-defined initial weightage factors $\theta$ corresponding to the plurality of features, the training dataset and a measure of error in fitting the cost function. Further, the computed cost function corresponding to the plurality of features are minimized based on a learning rate ($\alpha$), a weightage factors $\theta_j$ for the plurality of features and the total number of iterations performed for the cost function. Further, a final weightage factors corresponding to the plurality of features are determined. Further, the determined qualitative estimate of the corrosion inhibitor (CI) concentration is compared with a reference corrosion inhibitor (CI) concentration of the classification model.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
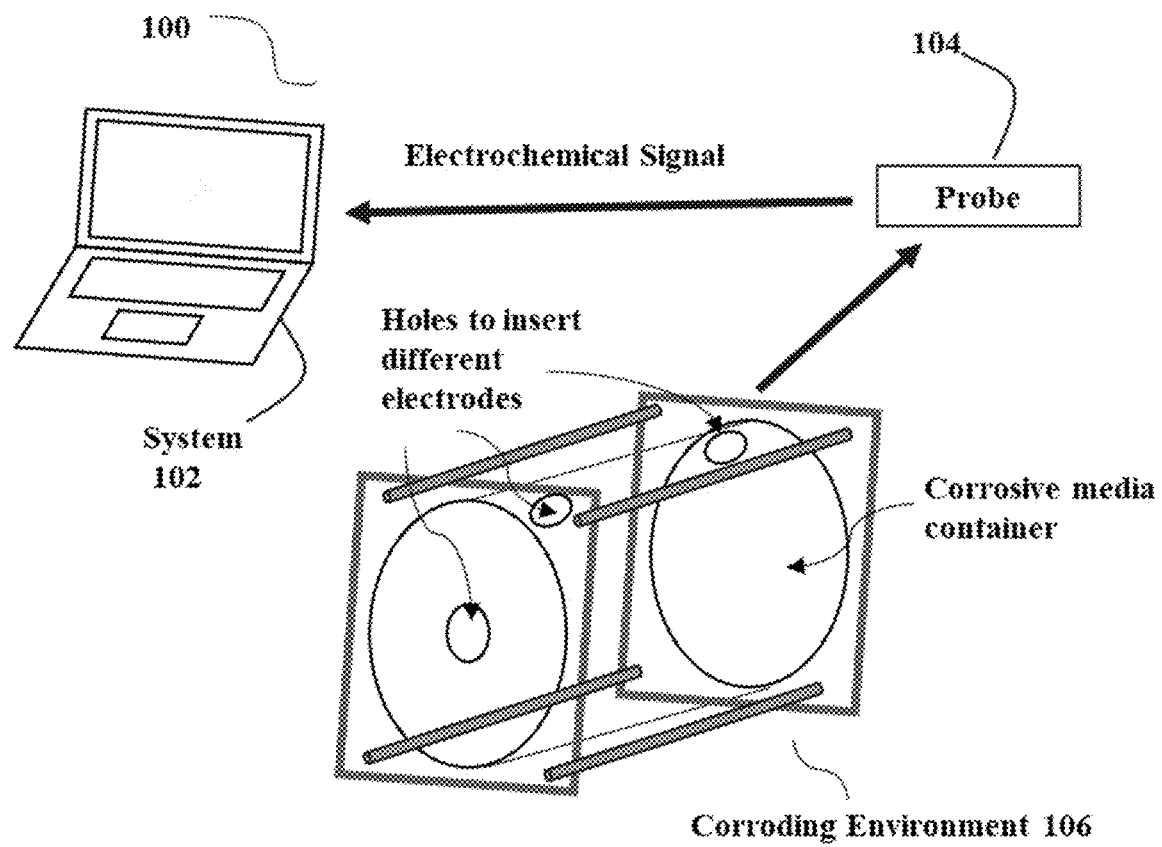
FIG. 1 illustrates an example corroding environment implementing a system, for estimating corrosion inhibitor (CI) concentration using a multielectrode array sensor, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provide a method and a system, for estimating corrosion inhibitor (CI) concentration using the multi-electrode array sensor. The disclosed method detects and estimates corrosion from the corroding environment in an indirect way. The disclosed method measures corrosion rate accurately from corroding environment for improving reliability and efficiency of engineering components by corrosion. The corroding environment may include liquid crude oil, natural gas, water pipelines, storage tanks and thereof where corrosion product is deposited. The method utilizes multi-electrode array sensor positioned in the corroding environment for capturing a plurality of electrochemical signals. Further, the method processes each electrochemical signal from the plurality of electrochemical signals for estimating the rate of corrosion in the corroding environment using a machine learning model. The machine learning model includes a regression model trained for determining the quantitative estimate of the corrosion inhibitor (CI) concentration and a classification model trained for determining the qualitative estimate of the corrosion inhibitor (CI) concentration. The disclosed method is further capable of estimating corrosion rate qualitatively and to quantify the corrosion rate and inhibitor concentration more accurately and efficiently. This disclosed method provides a low-cost robust method to and determining corrosion inhibitor (CI) concentration sensing. An example of the said system for corrosion rate estimation is described with the disclosed method in conjunction with FIGS. 1 to 6 below.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

FIG. 1 illustrates an example corroding environment implementing a system, for estimating corrosion inhibitor (CI) concentration using a multielectrode array sensor, in accordance with some embodiments of the present disclosure. As depicted in the example herein, the system 102 is configured to receive the plurality of electrochemical signals from the corroding environment using the multi-electrode array sensor. The corroding environment 106 includes a corrosive media container, wherein the corrosive media container is utilized for positioning the multi-electrode array sensor for capturing the plurality of electrochemical signals. Here, the multi-electrode array sensor includes a sensing or working electrode, a reference electrode and a counter electrode. The system 102 further analyses the plurality of electrochemical signals using the machine learning model. The system 102 is further explained in detail in conjunction with functional modules of FIG. 2 and flow diagram FIG. 3 for estimating the corrosion inhibitor (CI) concentration from the corroding environment.

Figure 2:
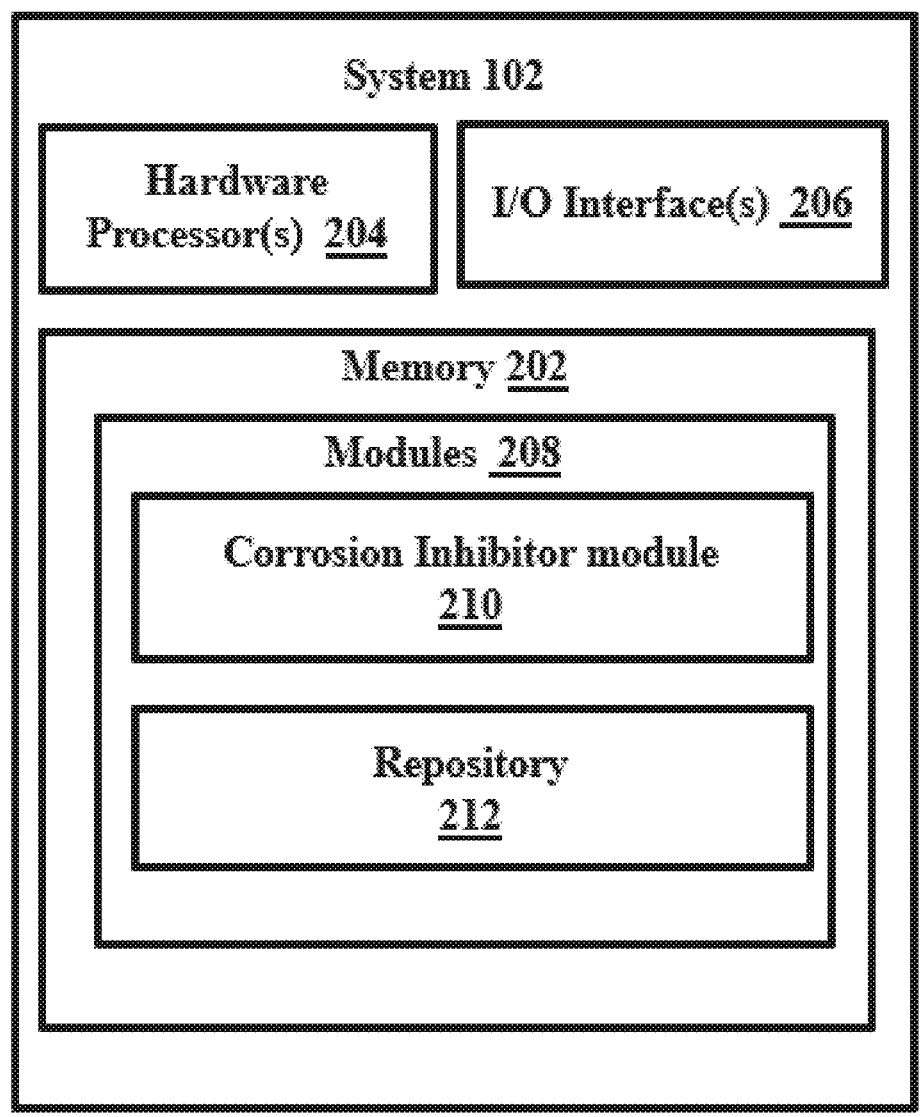
FIG. 2 illustrates a functional block diagram of the system of FIG. 1, in accordance with some embodiments of the present disclosure.

FIG. 2 illustrates a functional block diagram of the system of FIG,1, in accordance with some embodiments of the present disclosure. In an embodiment, the system 100 In an embodiment, the system 100 includes processor (s) 204, communication interface device(s), alternatively referred as or input/output (I/O) interface(s) 206, and one or more data storage devices or memory 208 operatively coupled to the processor (s) 204. The processor (s) 204 may be alternatively referred as one or more hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) 204 is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface(s) 206 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server for verifying software code.

The memory 202 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 202 further may include modules 208. In an embodiment, the modules 208 includes a corrosion inhibitor module 210, for implementing functions of the system 102. In an embodiment, the modules 208 can be an Integrated Circuit (IC) (not shown), external to the memory 202, implemented using a Field-Programmable Gate Array (FPGA) or an Application-Specific Integrated Circuit (ASIC). The names (or expressions or terms) of the modules of functional block within the modules 208 referred herein, are used for explanation and are not construed to be limitation(s). Further, the memory 202 can also include the repository 212. The repository 212 may store the training data, wherein the training data is collected based on the experimental results performed by the subject expert. The memory 202 may further comprise information pertaining to input(s)/output(s) of each step performed by the system 100 and methods of the present disclosure. The method involves utilizing the training data for processing the plurality of electrochemical signals using the disclosed method that will be explained with reference to the accompanying diagrams FIG. 3 and FIG. 4.

Figure 3:
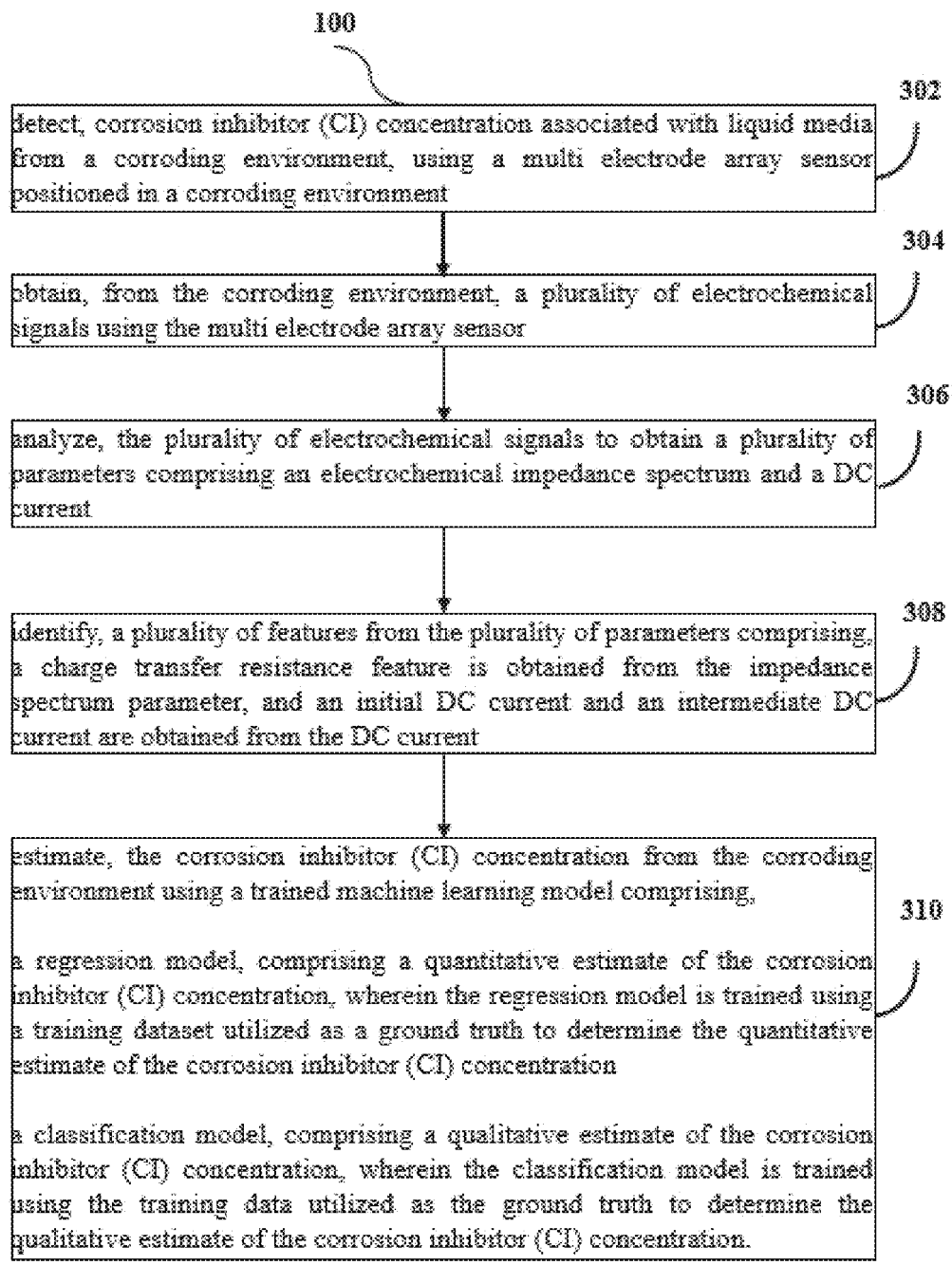
FIG. 3 is a flow diagram illustrating a method for estimating corrosion inhibitor (CI) concentration using the system of FIG. 1 functionally described in FIG. 2, in accordance with some embodiments of the present disclosure.

FIG. 3 is a flow diagram illustrating a method for estimating corrosion inhibitor (CI) concentration using the system of FIG. 1 functionally described in FIG. 2, in accordance with some embodiments of the present disclosure.

Figure 4:
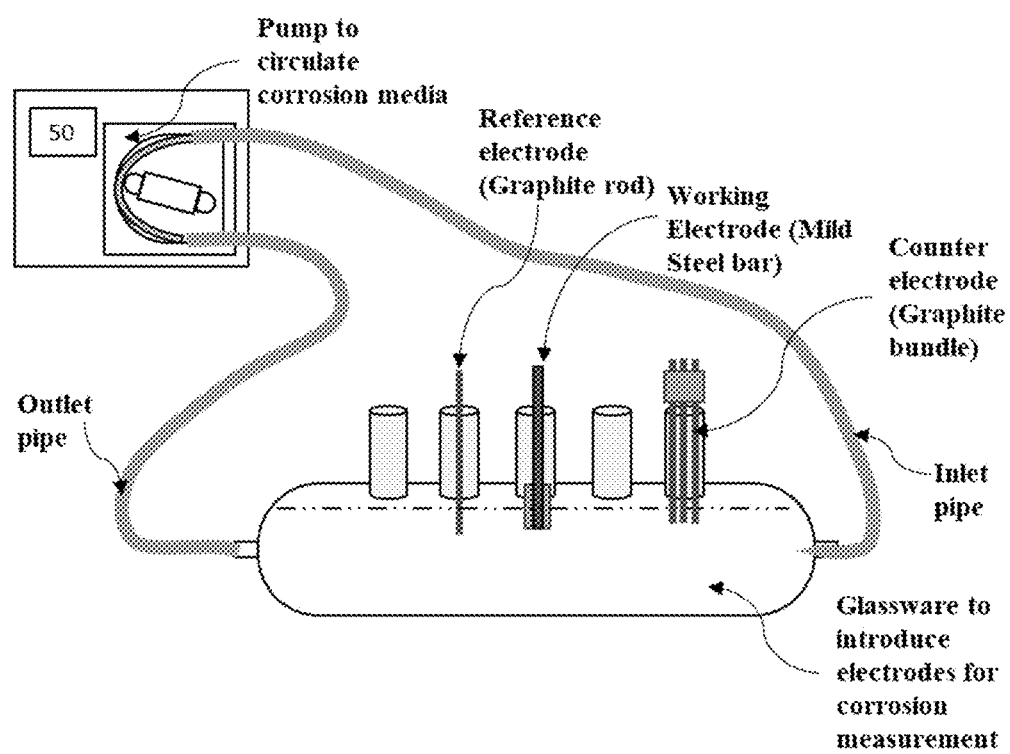
FIG. 4 illustrates example corroding environment for estimating corrosion inhibitor (CI) concentration using the system of FIG. 1, in accordance with some embodiments of the present disclosure.

The steps of the method 300 of the flow diagram will now be explained with reference to the components or blocks of the system 100 in conjunction with the example architecture of the system as depicted in FIG. 4. Here, FIG. 4 is illustrates example corroding environment for estimating corrosion inhibitor (CI) concentration using the system of FIG. 1, in accordance with some embodiments of the present disclosure. In an embodiment, the system 100 comprises one or more data storage devices or the memory 202 operatively coupled to the one or more processors 204 and is configured to store instructions for execution of steps of the method 300 by the one or more processors 204. In an embodiment, the corrosion inhibitor module 210 in the memory 202 store instructions for execution of steps of the method 300 by the one or more processors 204, for estimating the CI concentration. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

At step 302 of the method 300, the processor 204 is configured to position, a multi-electrode array sensor in a corroding environment for estimating a corrosion inhibitor (CI) concentration associated with a liquid media from the corroding environment. Referring now to FIG. 4 depicting an example, wherein the system is configured to position the multi-electrode sensor array. The multi-electrode array sensor array captures the plurality of electrochemical signals from the corroding environment which is circulated through a glassware. Through the holes of the glassware the electrodes are inserted and fixed in the corroding environment. The flow of corrosive liquid media is done by a pump connected to the glassware externally. There is an inlet pipe and an outlet pipe for the flow of the corrosive media. In one embodiment, the mild steel material is used forsensing working electrode, a graphite stick or Ag—AgCI type electrode for reference electrode and Pt mesh or graphite stick bundle for counter electrode that can be used for making different kinds of electrodes. Here, the working electrode (8 mm×8 mm square bar) is designed using the mild steel. The working electrode square bars are embedded into an epoxy resin mount. The counter electrode is a bundle of graphite rods for example. These electrodes are connected to electrical wires by clips, which lead the electrochemical output to be measured by potentiostat device. The corrosion inhibitor (CI) concentration module of the corrosion inhibitor (CI) system determines the presence of corrosion inhibitor in a pipeline using the designed multi-electrode array as sensor. The lab scale experiments are utilized to establish correlations between corrosion inhibitor (CI) concentration and rate of corrosion for each metallic electrode of at least one type of metal, alloy and thereof.

At step 304 of the method 300, the processor 204 is configured to obtain, the plurality of electrochemical signals from the corroding environment using the multi-electrode array sensor. The multi-electrode array sensor transmits the plurality of electrochemical signals dynamically using the probe. This multi-electrode array is designed using specific materials for detecting the rate of corrosion accurately. The sensing or working electrode of the multi-electrode array sensor is made of mild steel. The reference electrode of the multi-electrode array sensor is made of graphite stick or Ag—AgCI type electrode. The counter electrode of the multi-electrode array sensor is made of Pt mesh or graphite stick bundle. The multi-electrode array sensor built by these materials provides low cost-effective implementation for industrial environment in both static and dynamic conditions. In an embodiment, the corrosion inhibitor sensor includes arrays of multi-electrode coupons for multi materials. The anodic electrodes includes many metallic elements and alloys like different grades of steels, non-ferrous alloys, complex concentrated alloys. The cathodic materials include a graphite, platinum, silver and thereof. Based on the measured plurality of electrochemical signals from multi-electrodes for multi materials under different corroding environment. The system further analyses each electrochemical signal of the multi-electrode array sensor deployed in the corroding environment where such applications may be experimented to determine the corrosion inhibitor (CI) concentration.

At step 306 of the method 300, the processor 204 is configured to analyze, the plurality of electrochemical signals to obtain a plurality of parameters comprising an electrochemical impedance spectra and a DC current vs time. The obtained electrochemical impedance spectra parameter is analyzed to obtain the feature $x_1$: Charge transfer resistance among a plurality of features.

Figure 5A:
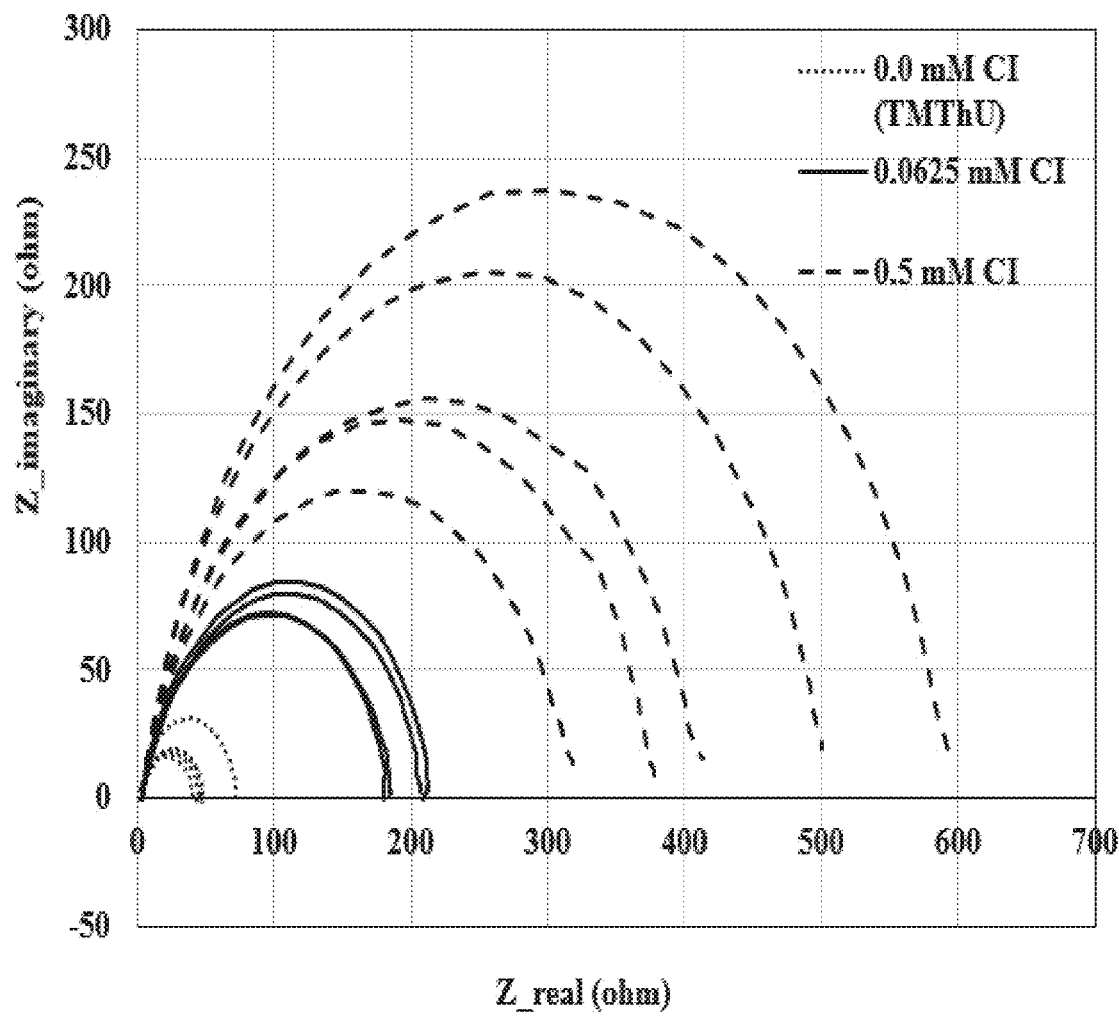
FIG. 5A illustrates graph of an electrochemical impedance spectra parameter obtained from a plurality of electrochemical signals detected from the corroding environment using the system of FIG. 1, in accordance with some embodiments of the present disclosure.

Referring now to FIG. 5A, which illustrates graph of an electrochemical impedance spectra parameter obtained from a plurality of electrochemical signals detected from the corroding environment using the system of FIG. 1, in accordance with some embodiments of the present disclosure. The X axis of the graph denotes the real part of the measured impedance and the Y axis is the imaginary part of the impedance. Measurements are done for different corrosion media with different degree of corrosion inhibitor (CI) concentrations (in milli molar unit). In this type of measurement, the electrochemical impedance is measured between the working electrode (WE) and the counter electrode (CE). The impedance between the working electrode (WE) and the counter electrode (CE) is measured with respect to the applied AC voltage frequencies. AC voltage applied is 0.01 V and the frequency used is in the range of 0.1 Hz-$10^5$ Hz.

Figure 5B:
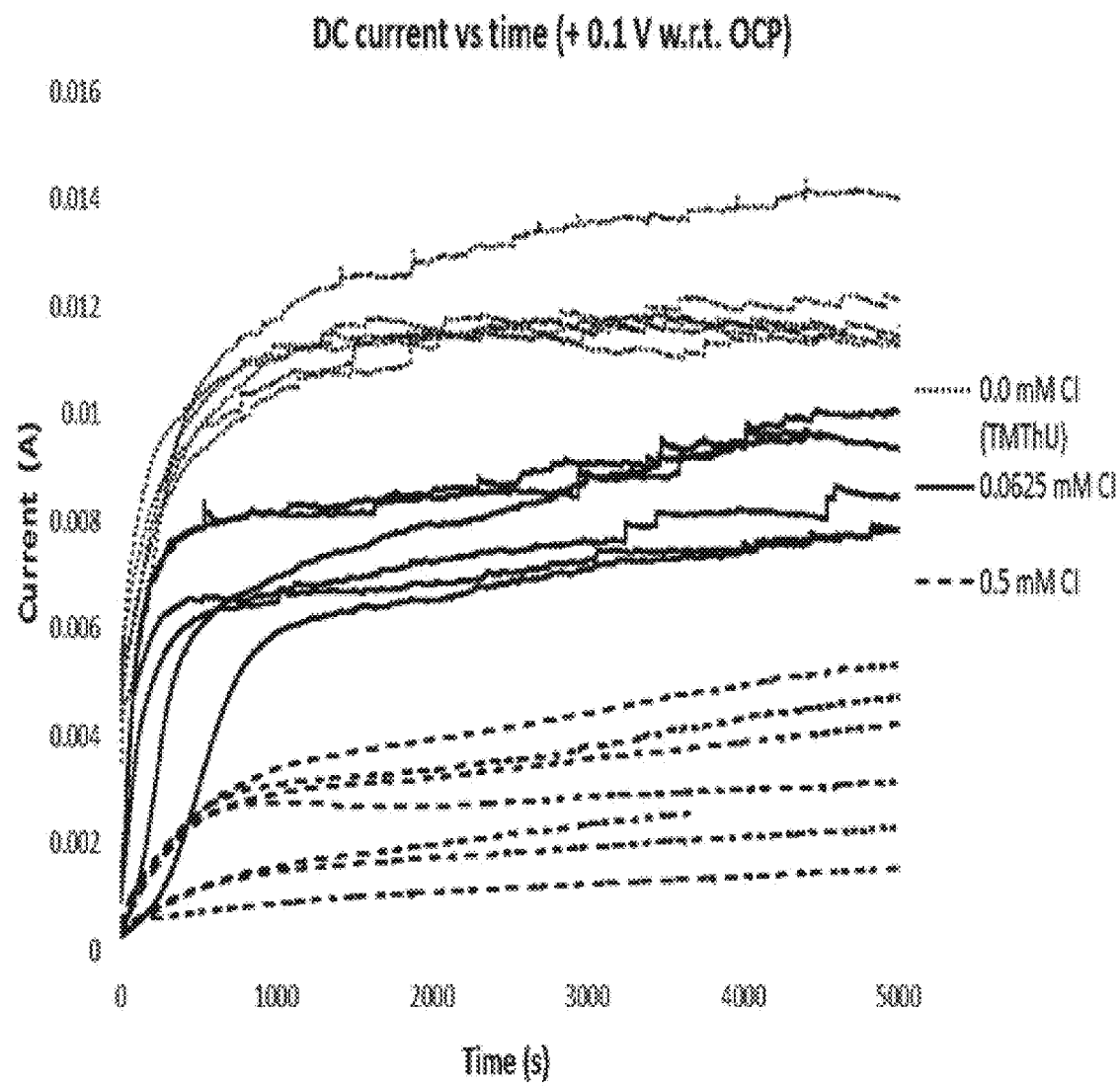
FIG. 5B illustrates graph of a DC current versus time obtained from the plurality of electrochemical signals detected from the corroding environment using the system of FIG. 1, in accordance with some embodiments of the present disclosure.

At step 308 of the method 300, the processor 204 is configured to identify, a plurality of features from the plurality of parameters comprising a charge transfer resistance feature is obtained from the impedance spectra parameter and an initial DC current and an intermediate DC current are obtained from the DC current. Referring now to FIG. 5B, illustrates graph of a DC current versus time obtained from the plurality of electrochemical signals detected from the corroding environment using the system of FIG. 1, in accordance with some embodiments of the present disclosure. This type of experiments involves applying a +0.1 V DC voltage into the working electrode with respect to the reference electrode. The DC current is measured at the counter electrode. The DC corrosion current is measured in total for more than an hour. Here, the DC current is measured at 10 second of elapsed time which is recorded as a feature "$x_2$: initial DC current" among the plurality of features. Then the average current between 2000-3000 seconds is taken as another feature as "$x_3$: intermediate DC current" among the plurality of features. As described, the FIG. 5B shows the DC corrosion current with time.

At step 310 of the method 300, the processor 204 is configured to estimate, the corrosion inhibitor (CI) concentration from the corroding environment using a trained machine learning model. The machine learning model includes the regression model and the classification model. In one embodiment, the regression model determines the quantitative estimate of the corrosion inhibitor (CI) concentration. Here, the regression model is trained using a training dataset utilized as a ground truth to determine the quantitative estimate of the corrosion inhibitor (CI) concentration. The training dataset is obtained by performing experiments repetitively. The $x_1$: Charge transfer resistance (obtained from EIS measurements), $x_2$: initial DC current (obtained from DC measurement) and $x_3$: intermediate DC current (obtained from DC measurement) are further inputted in the regression model training data. The training dataset is generated based on the experimental data or readings recorded using the multi-electrode array sensor inside the pipeline of the corroding environment. These experimental data or readings of corrosion rate or impedance are obtained based on the electrochemical outputs from the electrodes in corrosion media containing different corrosion inhibitor (CI) concentrations. The regression model is trained by obtaining, the plurality of features comprising the charge transfer resistance feature, the initial DC current and the intermediate DC current. Here, the plurality of features are obtained, $x_0$: bias term=1
$x_1$: charge transfer resistance
$x_2$: initial DC current
$x_3$: intermediate DC current The reference corrosion inhibitor (CI) concentration for the regression model varies between 0-0.5 mM (in milli molar unit) which is determined based on the experimental data.

Further, the model determines, the corrosion inhibitor (CI) concentration which is the quantitative estimate from the plurality of features by performing the following steps. The model further computes, a cost function using a pre-defined initial weightage factor 8 of value zero corresponding to the plurality of features, the training dataset and measure of error for fitting the cost function as represented below in equation 1 and equation 2, Model Fitted:

Corrosion inhibitor (CI) concentration (mM)=$h_\theta(X)$=
$\theta_0 \cdot x_0 + \theta_1 \cdot x_1 + \theta_2 \cdot x_2 + \theta_3 \cdot x_3 + \theta_4 \cdot x_1 \cdot x_2 + \theta_5 \cdot x_2 \cdot x_3 \theta_6 \cdot x_3 \cdot x_1$ (1)

The θ parameter denotes the weightage factors o the respective features. $h_\theta(X)$ is called the hypothesis of the regression model.

$$\text{Cost function formula: } J = \frac{1}{2m}\sum_{i=1}^{m}(h_\theta(X^i) - y^i)^2 \quad (2)$$

m is the number of experiments in the training set, $y^i$ is the corresponding experimental CI concentration, J is the cost function or measure of the error in data fitting.

The computed cost function corresponding to the plurality of features is minimized based on a learning rate α, a weightage factors $\theta_j$ for the plurality of features and the total number of iterations performed for the cost function as represented below in equation 3, $$\text{Cost function minimization: } \theta_j = \theta_j - \alpha * \frac{\partial J(\theta)}{\partial \theta_j} \quad (3)$$

Figure 6:
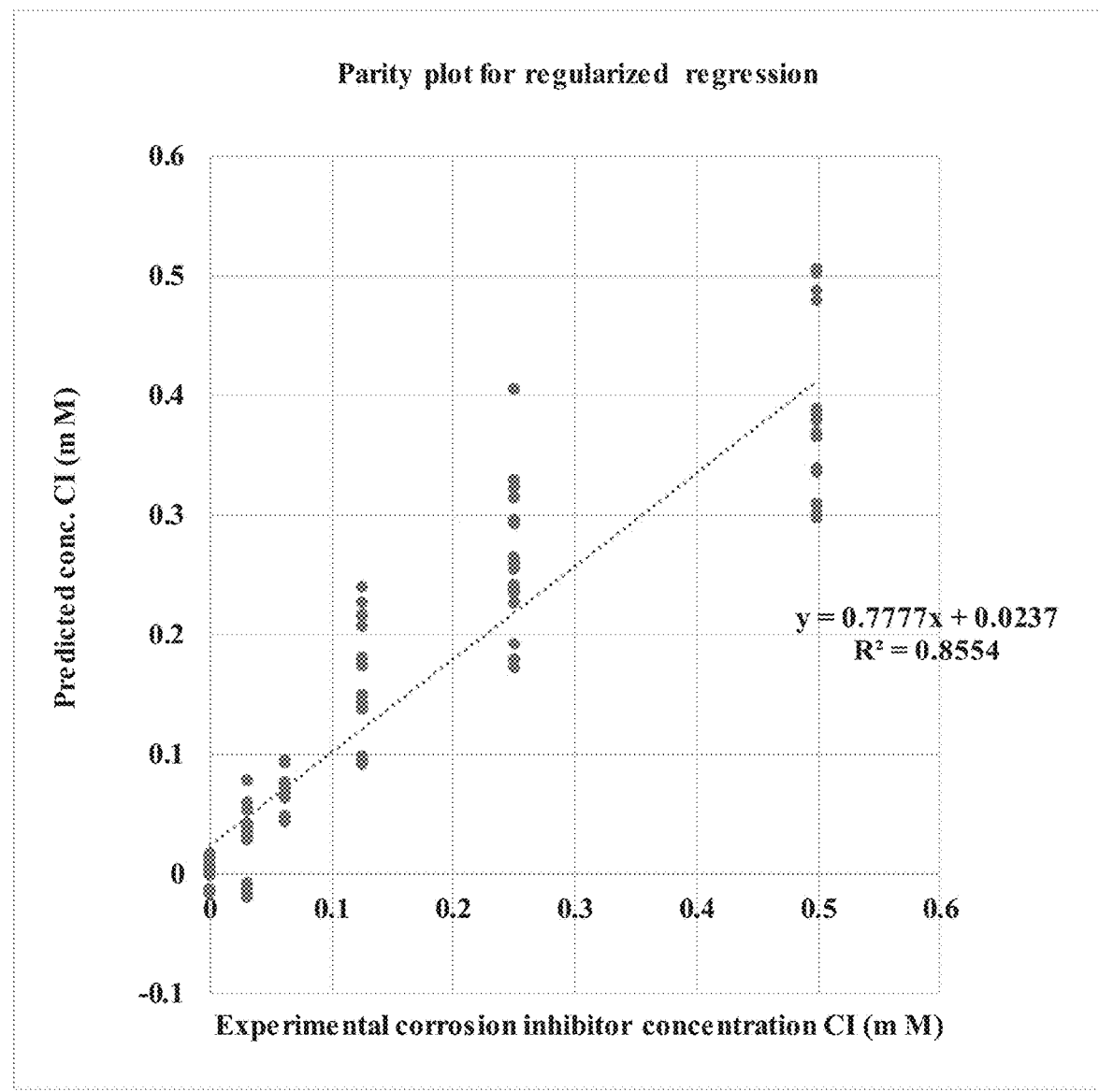
FIG. 6 depicts graph of regularized regression model for predicting corrosion inhibitor (CI) concentration in comparison with experimental results using the system of FIG. 1, for the plurality of detected electrochemical signals, in accordance with some embodiments of the present disclosure.

The weightage factors $\theta_j$ to the features are changed by the above formula for the model for correct regression prediction. α is called the learning rate of the machine learning method. The $\theta_j$ weightage factors are refined by multiple iterations. Further, the model determines, the final weightage factors corresponding to the plurality of features. Referring now to FIG. 6 which depicts graph of regularized regression model for predicting corrosion inhibitor (CI) concentration in comparison with experimental results using the system of FIG. 1, for the plurality of detected electrochemical signals, in accordance with some embodiments of the present disclosure. The parity plot figure shows the validity of the developed nonlinear regression model predictions performed on test data set. The regularization treatment is included in the prediction analysis. The $R^2$ score is 0.8554, which can be taken as a measure of the accuracy for the disclosed method of the ML model. Further, the corrosion inhibitor (CI) concentration corresponding to the plurality of features is compared based on the determined corrosion inhibitor (CI) concentration with the reference corrosion inhibitor (CI) concentration. The reference corrosion inhibitor (CI) concentration for the classification model varies between 0-6.0 mM (in milk molar unit).

In one embodiment, the corrosion inhibitor (CI) concentration from the plurality of features using the classification model. The classification model is the qualitative estimate of the corrosion inhibitor (CI) concentration, wherein the classification model is trained using the training dataset utilized as the ground truth to determine the qualitative estimate of the corrosion inhibitor (CI) concentration. The classification model obtains the plurality of features comprising the charge transfer resistance feature, the initial DC current and the intermediate DC current from the plurality of parameters. The corrosion inhibitor (CI) concentration determines the qualitative estimate from the plurality of features by, computing, the cost function using a logistic function, the pre-defined initial weightage factors θ corresponding to the plurality of features, the training dataset and the measure of error in fitting the cost function as described in equation 3 and equation 4,
Model Fitted:

Corrosion inhibitor (CI) concentration (mM)=$h_\theta(X)$=
$1/(1+e^{-z})$; $z=\theta_0.x_0+\theta_1.x_1+\theta_2.x_2\theta_3.x_3$; if $h_\theta(X)>$
0.5 then the result is yes, otherwise no    (3)

The θ parameter denotes the weightage factors of the respective features. $h_\theta(X)$ is called the hypothesis of the classification model.
Cost Function Formula:

$$J = -\frac{1}{m}\sum_{i=1}^{m}(y(i)\cdot\log(h\theta(x(i)) + (1-y(i))\cdot\log(1-h\theta(x(i)))) \quad (4)$$

$y^{(i)}$ is 1 if the experimental result is taken as "yes", otherwise it is zero. The computed cost function corresponding to the plurality of features is minimized based on the learning rate (α), the weightage factors $\theta_j$ for the plurality of features and the total number of iterations performed for the cost function as represented below in equation 5, $$\text{Cost function minimization: } \theta_j := \theta_j - \alpha \cdot \frac{\partial J(\theta)}{\partial \theta_j} \quad (5)$$

determining, the final weightage factors corresponding to the plurality of features. Further the corrosion inhibitor (CI) concentration corresponding to the plurality of features is compared based on the reference experimentally determined corrosion inhibitor (CI) concentration. The classification model is performed iteratively for the classification model trials between 10-15 times for varying corrosion inhibitor (CI) concentration as depicted below in table 1,

TABLE 1

Classification model - Corrosion Inhibitor (CI) concentration

| Classification model Corrosion inhibitor (CI) concentartion | Accuracy |
| --- | --- |
| <0.03125 m M (4.1 ppm level) | 98.1% |
| <0.0625 m M (8.25 ppm level) | 98.9% |
| <0.25 m M (33 ppm level) | 94.0% |

The written description describes the subject matter herein to enable any person skilled in the art to make and use the embodiments. The scope of the subject matter embodiments is defined herein and may include other modifications that occur to those skilled in the art. Such other modifications are intended to be within the scope of the present disclosure if they have similar elements that do not differ from the literal language of the embodiments or if they include equivalent elements with insubstantial differences from the literal language of the embodiments described herein.

The embodiments of the present disclosure herein addresses unresolved problem of estimating corrosion inhibitor (CI) concentration using multi-electrode array sensor. This disclosed method detects qualitative and quantitative estimate of corrosion inhibitor (CI) concentration in real time industrial environments. This method provides a low cost, reliable, efficient and accurate detection of corrosion inhibitor (CI) concentration using the designed multi-electrode array sensors. Further, the method receives the plurality of electrochemical signals using the multi-electrode array sensor. The plurality of electrochemical signals are analysed for identifying the plurality of features from the plurality of parameters. The corrosion inhibitor (CI) concentration from the plurality of features are estimated using the trained machine learning model, comprising the regression model and the classification model. The method provides high end chemical analysis equipment required for estimating the corrosion inhibitor (CI) concentration in the corroding environment.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein, Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method (300) for estimating corrosion inhibitor (CI) concentration, wherein the method comprises:
   positioning (302), via the one or more hardware processors, a multi-electrode array sensor in a corroding environment for estimating a corrosion inhibitor (CI) concentration associated with a liquid media from the corroding environment, wherein the liquid media from the corroding environment is circulated externally into glassware by a pump, wherein the glassware contains holes to insert and fix the multi-electrode array sensor into the liquid media for in-situ estimation of CI concentration of the corroding environment;
   obtaining (304), via the one or more hardware processors, from the corroding environment, a plurality of electrochemical signals using the multi-electrode array sensor, wherein the plurality of electrochemical signals are obtained using the multi-electrode array sensor having a sensing working electrode made of mild steel, a reference electrode made of a graphite stick or Ag—AgCl type electrode, and a counter electrode made of Pt mesh or graphite stick bundle, wherein the plurality of electrochemical signals is obtained by applying +0.1 V DC voltage into the working electrode with respect to the reference electrode, and a DC current is measured at the counter electrode;
   analyzing (306), via the one or more hardware processors, the plurality of electrochemical signals to obtain a plurality of parameters comprising an electrochemical impedance spectra and a DC current versus time;
   identifying (308), via the one or more hardware processors, a plurality of features from the plurality of parameters comprising:
     a charge transfer resistance feature obtained from the electrochemical impedance spectra parameter, and
     an initial DC current and an intermediate DC current obtained from the DC current versus time, wherein the initial DC current is measured at a predetermined elapsed time of 10 seconds, and the intermediate DC current is measured as an average DC current between a predetermined time range of 2000 to 3000 seconds;
   estimating (310), via the one or more hardware processors, the corrosion inhibitor (CI) concentration from the plurality of features using a trained machine learning model comprising,
     a regression model determining a quantitative estimate of the corrosion inhibitor (CI) concentration, wherein the regression model is trained using a training dataset utilized as a ground truth to determine the quantitative estimate of the corrosion inhibitor (CI) concentration, wherein training the regression model for determining the quantitative estimate of the corrosion inhibitor (CI) concentration comprises:
       determining a reference corrosion inhibitor (CI) concentration for the regression model based on the training dataset, wherein the reference corrosion inhibitor (CI) concentration for the regression model varies between 0-0.5 mM (in milli molar unit);
       computing a cost function using a pre-defined initial weightage factor $\theta$ corresponding to the plurality of features, the training dataset, and a measure of error for fitting the cost function to the reference corrosion inhibitor (CI) concentration of the regression model;
       minimizing the computed cost function corresponding to the plurality of features, based on a learning rate $\alpha$, a weightage factors $\theta j$ for the plurality of features and the total number of iterations performed for the cost function;
       determining a final weightage factors corresponding to the plurality of features; and
       determining the quantitative estimate of the corrosion inhibitor (CI) of the plurality of features using the final weightage factors; and
     a classification model determining a qualitative estimate of the corrosion inhibitor (CI) concentration, wherein the classification model is trained using the training dataset utilized as the ground truth to determine the qualitative estimate of the corrosion inhibitor (CI) concentration, wherein training the classification model for determining the qualitative estimate of the corrosion inhibitor (CI) concentration comprises:
       determining a reference corrosion inhibitor (CI) concentration for the classification model based on the training dataset, wherein the reference corrosion inhibitor concentration for the classification model varies between 0-6.0 mM (in milli molar unit);
       computing a cost function using a logistic function, a pre-defined initial weightage factors $\theta$ corresponding to the plurality of features, the training dataset and a measure of error for fitting the cost function to the reference corrosion inhibitor (CI) concentration of the classification model;
       minimizing the computed cost function corresponding to the plurality of features, based on a learning rate ($\alpha$), a weightage factors $\theta j$ for the plurality of features and the total number of iterations performed for the cost function;
       determining a final weightage factors corresponding to the plurality of features; and
       determining the qualitative estimate of the corrosion inhibitor (CI) of the plurality of features using the final weightage factors.

2. The method as claimed in claim 1, wherein the corrosion inhibitor concentration for any unknown liquid is estimated using the corrosion inhibitor concentration range of the regression model.

3. The method as claimed in claim 1, wherein the corrosion inhibitor concentration for any unknown liquid is estimated using the corrosion inhibitor concentration range of the classification model.

4. A system (102) for electrical load disaggregation, the system (102) comprising:
a memory (202) storing instructions;
one or more Input/Output (I/O) interfaces (206);
and one or more hardware processors (204) coupled to the memory (202) via the one or more I/O interfaces (206), wherein the one or more hardware processors (204) are configured by the instructions to:
position a multi-electrode array sensor in a corroding environment for estimating a corrosion inhibitor (CI) concentration associated with a liquid media from the corroding environment, wherein the liquid media from the corroding environment is circulated externally into a glassware by a pump, wherein the glassware contains holes and fix to insert the multi-electrode array sensor into the liquid media for in-situ estimation of CI concentration of the corroding environment;
obtain from the corroding environment, a plurality of electrochemical signals using the multi-electrode array sensor, wherein the plurality of electrochemical signals are obtained using the multi-electrode array sensor having a sensing working electrode made of mild steel, a reference electrode made of a graphite stick or Ag—AgCI type electrode, and a counter electrode made of Pt mesh or graphite stick bundle, wherein the plurality of electrochemical signals is obtained by applying +0.1 V DC voltage into the working electrode with respect to the reference electrode, and a DC current is measured at the counter electrode;
analyze the plurality of electrochemical signals to obtain a plurality of parameters comprising an electrochemical impedance spectra and a DC current versus time;
identify a plurality of features from the plurality of parameters comprising:
a charge transfer resistance feature is obtained from the electrochemical impedance spectra parameter,
an initial DC current and an intermediate DC current are obtained from the DC current vs time, wherein the initial DC current is measured at a predetermined elapsed time of 10 seconds, and the intermediate DC current is measured as an average DC current between a predetermined time range of 2000 to 3000 seconds; and
estimate the corrosion inhibitor (CI) concentration from the plurality of features using a trained machine learning model comprising,
a regression model determining a quantitative estimate of the corrosion inhibitor (CI) concentration, wherein the regression model is trained using a training dataset utilized as a ground truth to determine the quantitative estimate of the corrosion inhibitor (CI) concentration, wherein training the regression model for determining the quantitative estimate of the corrosion inhibitor (CI) concentration comprises:
determining a reference corrosion inhibitor (CI) concentration for the regression model based on the training dataset, wherein the reference corrosion inhibitor (CI) concentration for the regression model varies between 0-0.5 mM (in millimolar unit);
computing a cost function using a pre-defined initial weightage factor $\theta$ corresponding to the plurality of features, the training dataset, and a measure of error for fitting the cost function to the reference corrosion inhibitor (CI) concentration of the regression model;
minimizing the computed cost function corresponding to the plurality of features, based on a learning rate $\alpha$, a weightage factors $\theta j$ for the plurality of features and the total number of iterations performed for the cost function;
determining a final weightage factors corresponding to the plurality of features; and
determining the quantitative estimate of the corrosion inhibitor (CI) of the plurality of features using the final weightage factors; and
a classification model determining a qualitative estimate of the corrosion inhibitor (CI) concentration, wherein the classification model is trained using the training dataset utilized as the ground truth to determine the qualitative estimate of the corrosion inhibitor (CI) concentration, wherein training the classification model for determining the qualitative estimate of the corrosion inhibitor (CI) concentration comprises:
determining a reference corrosion inhibitor (CI) concentration for the classification model based on the training dataset, wherein the reference corrosion inhibitor concentration for the classification model varies between 0-6.0 mM (in millimolar unit);
computing a cost function using a logistic function, a pre-defined initial weightage factors $\theta$ corresponding to the plurality of features, the training dataset and a measure of error for fitting the cost function to the reference corrosion inhibitor (CI) concentration of the classification model;
minimizing the computed cost function corresponding to the plurality of features, based on a learning rate ($\alpha$), a weightage factors $\theta j$ for the plurality of features and the total number of iterations performed for the cost function;
determining a final weightage factors corresponding to the plurality of features; and
determining the qualitative estimate of the corrosion inhibitor (CI) of the plurality of features using the final weightage factors.

5. The system (102) as claimed in claim 4, wherein the corrosion inhibitor concentration for any unknown liquid is estimated using the corrosion inhibitor concentration range of the regression model.

6. The system (102) as claimed in claim 4, wherein the corrosion inhibitor concentration for any unknown liquid is estimated using the corrosion inhibitor concentration range of the classification model.

7. One or more non-transitory machine-readable information storage mediums comprising one or more instructions which when executed by one or more hardware processors perform actions comprising:
positioning (302), via the one or more hardware processors, a multi-electrode array sensor in a corroding environment for estimating a corrosion inhibitor (CI) concentration associated with a liquid media from the corroding environment, wherein the liquid media from the corroding environment is circulated externally into a glassware by a pump, wherein the glassware contains holes to insert and fix the multi-electrode array sensor into the liquid media for in-situ estimation of CI concentration of the corroding environment;

obtaining (304), via the one or more hardware processors, from the corroding environment, a plurality of electrochemical signals using the multi-electrode array sensor, wherein the plurality of electrochemical signals are obtained using the multi-electrode array sensor having a sensing working electrode made of mild steel, a reference electrode made of a graphite stick or Ag—AgCl type electrode, and a counter electrode made of Pt mesh or graphite stick bundle, wherein the plurality of electrochemical signals is obtained by applying +0.1 V DC voltage into the working electrode with respect to the reference electrode, and a DC current is measured at the counter electrode;

analyzing (306), via the one or more hardware processors, the plurality of electrochemical signals to obtain a plurality of parameters comprising an electrochemical impedance spectra and a DC current versus time;

identifying (308), via the one or more hardware processors, a plurality of features from the plurality of parameters comprising:
　a charge transfer resistance feature obtained from the electrochemical impedance spectra parameter, and
　an initial DC current and an intermediate DC current obtained from the DC current versus time, wherein the initial DC current is measured at a predetermined elapsed time of 10 seconds, and the intermediate DC current is measured as an average DC current between a predetermined time range of 2000 to 3000 seconds; and estimating (310), via the one or more hardware processors, the corrosion inhibitor (CI) concentration from the plurality of features using a trained machine learning model comprising,
　a regression model determining a quantitative estimate of the corrosion inhibitor (CI) concentration, wherein the regression model is trained using a training dataset utilized as a ground truth to determine the quantitative estimate of the corrosion inhibitor (CI) concentration, wherein training the regression model for determining the quantitative estimate of the corrosion inhibitor (CI) concentration comprises:
　　determining a reference corrosion inhibitor (CI) concentration for the regression model based on the training dataset, wherein the reference corrosion inhibitor (CI) concentration for the regression model varies between 0-0.5 mM (in milli molar unit);
　　computing a cost function using a pre-defined initial weightage factor $\theta$ corresponding to the plurality of features, the training dataset, and a measure of error for fitting the cost function to the reference corrosion inhibitor (CI) concentration of the regression model;
　　minimizing the computed cost function corresponding to the plurality of features, based on a learning rate $\alpha$, a weightage factors $\theta j$ for the plurality of features and the total number of iterations performed for the cost function;
　　determining a final weightage factors corresponding to the plurality of features; and
　　determining the quantitative estimate of the corrosion inhibitor (CI) of the plurality of features using the final weightage factors; and
　a classification model determining a qualitative estimate of the corrosion inhibitor (CI) concentration, wherein the classification model is trained using the training dataset utilized as the ground truth to determine the qualitative estimate of the corrosion inhibitor (CI) concentration, wherein training the classification model for determining the qualitative estimate of the corrosion inhibitor (CI) concentration comprises:
　　determining a reference corrosion inhibitor (CI) concentration for the classification model based on the training dataset, wherein the reference corrosion inhibitor concentration for the classification model varies between 0-6.0 mM (in millimolar unit);
　　computing a cost function using a logistic function, a pre-defined initial weightage factors $\theta$ corresponding to the plurality of features, the training dataset and a measure of error for fitting the cost function to the reference corrosion inhibitor (CI) concentration of the classification model;
　　minimizing the computed cost function corresponding to the plurality of features, based on a learning rate $(\alpha)$, a weightage factors $\theta j$ for the plurality of features and the total number of iterations performed for the cost function;
　　determining a final weightage factors corresponding to the plurality of features; and
determining the qualitative estimate of the corrosion inhibitor (CI) of the plurality of features using the final weightage factors.

* * * * *